(12) United States Patent
Schwartz et al.

(10) Patent No.: US 8,420,054 B2
(45) Date of Patent: Apr. 16, 2013

(54) NONINVASIVE METHOD FOR MEASURING HISTAMINE FROM SKIN AS AN OBJECTIVE MEASUREMENT OF ITCH

(75) Inventors: James Robert Schwartz, West Chester, OH (US); Kathleen Marie Kerr, Okeana, OH (US); Patricia West Doyle, Cincinnati, OH (US); Kenneth Robert Wehmeyer, Cincinnati, OH (US); Thomas Massey Burt, Middletown, OH (US); Angela Marie Fieno, Hamilton, OH (US); Rohan Lalith Wimalasena, Mason, OH (US); Gina Marie Fadayel, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 749 days.

(21) Appl. No.: 12/562,757

(22) Filed: Sep. 18, 2009

(65) Prior Publication Data

US 2011/0071123 A1    Mar. 24, 2011

(51) Int. Cl.
*A61K 49/00* (2006.01)
(52) U.S. Cl.
USPC .............................. 424/9.1; 424/9.2; 424/9.8
(58) Field of Classification Search .................. None
See application file for complete search history.

(56) References Cited

U.S. PATENT DOCUMENTS

| | | | |
|---|---|---|---|
| 3,900,558 | A | 8/1975 | Kinsolving |
| 4,869,875 | A | 9/1989 | Skov et al. |
| 5,047,330 | A | 9/1991 | Grassi et al. |
| 6,420,168 | B1 | 7/2002 | Takeshita et al. |
| 2007/0243625 | A1 | 10/2007 | Oguri |

OTHER PUBLICATIONS

Lawlor F et al: "Symptomatic Dermographism Wealing Mast Cells and Histamine are Decreased in the Skin Following Long-Term Application of a Potent Topical Corticosteroid", British Journal of Dermatology, vol. 121, No. 5, 1989, pp. 629-634.
Perkins MA A et al: "A non-invasive tape absorption method for recovery of inflammatory mediators to differentiate normal from compromised scalp conditions."; 7 pages, 2002.
Sawleshwarkar S N et al: "Multicenter, open-label, non-comparative study of a combination of polytar and zinc pyrithione shampoo in the management of dandruff",Indian Journal of Dermatology, Venereology and Leprology, vol. 70, No. 1, 2004, pp. 25-28.
Granerus G EI al: "Studies on histamine metabolism in mastocytosis. ", The Journal of Investigative Dermatology, vol. 80, No. 5, 1983, pp. 410-416.
Harding, C., A. Moore, J. Rogers, H. Meldrum, et al., Dandruff: a condition characterized by decreased levels of intercellular lipids in scalp stratum corneum and impaired barrier function. Arch. Dermatol. Res., 2002. 294: p. 221-230.
Redinbaugh, M.G. and Turley, R.B. (1986). "Adaptation of the bicinchoninic acid protein assay for use with microtiter plates and sucrose gradient fractions." Anal.Biochem. 153, 267-271.
Harvima, I.T. et al "Is There a Role for Mast Cells in Psoriasis?"; Arch Dermatol (2008) 300:461-478.
Heinemann, C. et al. "Efficacy Measurement of Topical Antihistamines"; Skin Pharmacol Appl Skin Physiol 2003; 16: 4-11.
Petersen, LJ et al, "Studies on Mast Cells and Histamine Release in Psoriasis: The Effect of Ranitidine", Acta Derm Venereol 78: 190-193, 1998.
Ikoma, A. et al., "Neuronal Sensitization for Histamine-Induced Itch in Lesional Skin of Patients with Atopic Dermatitis", Arch Dermatol. Nov. 2003; 1455-1458.
Y. Ashida et al., "Dry Environment Increases Mast Cell Number and Histamine Content in Dermis in Hairless Mice", British Journal of Dermatology 2003; 149; 240-247.
M. Kobayashi, et al. "Expression of Toll-Like Receptor 2, NOD2 and Dectin-1 and Stimulatory Effects of Their Ligands and Histamine in Normal Human Keratinocytes"; British Journal of Dermatology, Feb. 2009; 160: 297-304.
Balaskas, E. et al., "Histamine and Serotonin As Markers of Uremic Pruritus", Clinical Chemistry. vol. 43, No. 6, Part 2, 1997; p. S113.
International Search Report, 11456-JC. International Application No. PCT/US2010/048185; Filing Date Sep. 9, 2010; 11 pages.
Gschwandtner, M. et al.; "Histamine Upregulates Keratinocyte MMP-9 Production via the Histamine H1 Receptor"; J. Invest Dermatol, Dec. 2008; 128 (12): 2783-91.

*Primary Examiner* — Debbie K Ware

(57) ABSTRACT

A method for measuring of histamine in an epidermis comprising applying an adhesive article to an epithelium of a mammal; allowing for adherence of epithelial cells to the adhesive article; removing the adhesive article from the epithelium of the mammal; preparing the adhesive article using standard laboratory methods for extraction; extracting histamine from the epithelial cells adhered to said adhesive article; measuring histamine from the epithelial cells adhered to said adhesive article; determining the amount of histamine in the epithelial cells as compared to a baseline sample. Further, a method of objectively measuring the perception of itch in mammals and wherein there is a reduction in histamine from a baseline level which is directly proportional to a reduction in an itch perception.

20 Claims, 6 Drawing Sheets

NONINVASIVE METHOD FOR MEASURING HISTAMINE FROM SKIN AS AN OBJECTIVE MEASUREMENT OF ITCH

FIELD OF THE INVENTION

The present invention relates to a method for measuring the amount of histamine from a skin sample and the objective link and correlation of the amount of histamine as it directly correlates to itch perception in mammals.

BACKGROUND OF THE INVENTION

The importance of the symptom of itch in scalp dermatitis has been evaluated in the past. The most frequently described condition associated with unhealthy scalp is itch. This is also the most bothersome symptom, having the largest negative influence on sufferers' quality of life.

With regard to the general physiology of itch, the perception of itch represents the end of a complex physiological pathway that is initiated at the skin surface. A number of stimuli can start the cascade of events that eventually lead to the perception of itch. The stimulus binds to specialized receptor cells in the dermis triggering the release of histamine. Histamine then binds to the nerve endings, starting an electrical pathway along the nerve fiber that is transferred along the spinal column until it is received in the brain and interpreted as itch.

In general, while there is a wide range of potential mediators of itch, histamine is considered the prototypical physiological chemical mediator of itch. Histamine is a small molecule amine that was shown in 1927 to be a natural constituent of skin tissue (hence the name from the Greek word for tissue, histos). Key support for the direct role of histamine in itch is that antihistamines can be very effective in relieving itch in some skin conditions. Another argument in favor of the role of histamine is that it can be used to experimentally induce itch.

For specific cases, the strength of the association between histamine and itch has been studied for a number of specific skin conditions. There is a very strong association between histamine levels and itch severity for conditions such as urticaria and insect bites. The association with atopic dermatitis is less well-defined. Higher histamine levels have been found in the skin of sufferers of eczema and psoriasis. Even dry skin has been found to result in higher histamine levels.

While the histamine levels in dandruff and seborrheic dermatitis have not been previously investigated, it is likely there is a strong relationship between the itch severity and histamine levels. First, psoriasis and dandruff share many common etiological features, making it likely that the established histamine-itch relationship in psoriasis will apply to dandruff as well. It has also been demonstrated [Harding, C., A. Moore, J. Rogers, H. Meldrum, et al., *Dandruff: a condition characterized by decreased levels of intercellular lipids in scalp stratum corneum and impaired barrier function*. Arch. Dermatol. Res., 2002. 294: p. 221-230.] that dandruff sufferers have an increased incidence of itch in response to topically applied histamine, demonstrating the physiological relevance of histamine in scalp itch associated with dandruff.

Alternative biomarkers which may serve as mediators for itch are Substance P, and cannabinoids. Other possible mediators are provided in Neurophysiology of Pruritus; Cutaneous Elicitation of Itch; Arch Dermatol./Vol. 139, November 2003 and incorporated by reference herein.

SUMMARY OF THE INVENTION

An embodiment of the present invention is directed to a method for measuring of histamine in an epidermis comprising applying an adhesive article to an epithelium of a mammal; allowing for adherence of epithelial cells to the adhesive article; removing the adhesive article from the epithelium of the mammal; preparing the adhesive article using standard laboratory methods for extraction; extracting histamine from the epithelial cells adhered to said adhesive article; measuring histamine from the epithelial cells adhered to said adhesive article; determining the amount of histamine in the epithelial cells as compared to a baseline sample.

A further embodiment of the present invention is a method of objectively measuring the perception of itch in mammals, said method comprising the steps of: applying as adhesive article to an epithelium of a mammal; allowing for the adherence of epithelial cells to the adhesive article; removing the adhesive article from the epithelium of the mammal; preparing the adhesive article using standard laboratory methods for extraction; extracting histamine from the epithelial cells adhered to said adhesive article; measuring histamine from the epithelial cells adhered to said adhesive article; and determining the amount of histamine in the epithelial cells as compared to a baseline sample.

These and other features, aspects, and advantages of the present invention will become evident to those skilled in the art from a reading of the present disclosure.

DETAILED DESCRIPTION OF THE INVENTION

Figure 1:
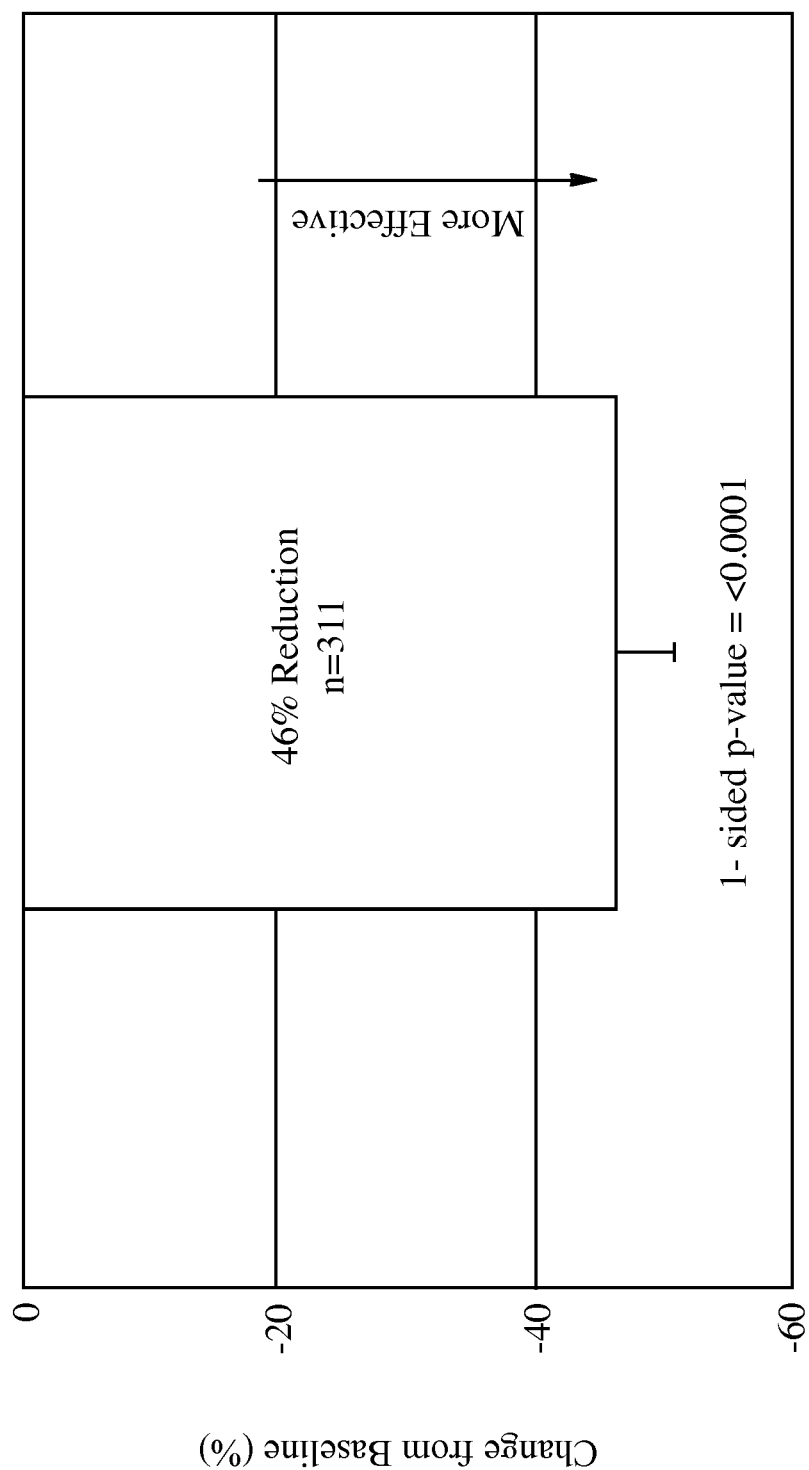
FIG. 1. This figure is a measurement of histamine reduction when compared to baseline following treatment with an anti-dandruff shampoo.

While the specification concludes with claims which particularly point out and distinctly claim the invention, it is believed the present invention will be better understood from the following description.

The present invention can comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

The components and/or steps, including those, which may optionally be added, of the various embodiments of the present invention, are described in detail below.

All documents cited are, in relevant part, incorporated herein by reference; the citation of any document is not to be construed as an admission that it is prior art with respect to the present invention.

All ratios are weight ratios unless specifically stated otherwise.

All temperatures are in degrees Celsius, unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more"

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

The term 'skin' means the outer covering of a vertebrate animal, consisting of two layers of cells, a thick inner layer (the dermis) and a thin outer layer (the epidermis). The epidermis is the external, nonvascular layer of the skin. It is made up, from within outward, of five layers of EPITHELIUM: (1) basal layer (stratum basale epidermidis); (2) spinous layer (stratum spinosum epidermidis); (3) granular layer (stratum granulosum epidermidis); (4) clear layer (stratum lucidum epidermidis); and (5) horny layer (stratum corneum epidermidis).

The term "sample" refers to any preparation from skin or epidermis of a subject.

The term "non-invasive" means a procedure that does not require insertion of an instrument or device through the skin or a body orifice for diagnosis or treatment.

The term "adhesive device" means a device used for the removal of the skin's epidermal layer by using an adhesive or an adhesive material on a substrate. For example, skin samples with adhesive tapes such as D-Squame® (polyacrylate ester adhesives; CuDerm; Dallas Tex.), Durapor, Sebutape™ (acrylic polymer films; CuDern; Dallas, Tex.), Tegaderm™, Duct tape (333 Duct Tape, Nashua tape products), Scotch® Tape (3M Scotch 810, St. Paul, Minn.), Diamond™ (The Sellotape Company; Eindhoven, the Netherlands), Sentega™ (polypropylene tape, Sentega Eiketten BV, Utrecht, The Netherlands) may be used. The adhesive may be any of the commonly used pressure-sensitive-type adhesives or those which solidify quickly upon skin content (such as cynaoacylates). The adhesives may be on flexible or solid backings to make sampling easier. A constant pressure device (e.g. Desquame Pressure Instrument, CuDerm; Dallas, Tex.) can be used to apply pressure to the adhesive device during sampling.

Samples from a tissue may be isolated by any number of means well known in the art. Invasive methods for isolating a sample include the use of needles, for example during blood sampling, as well as biopsies of various tissues, blistering techniques and laser poration. Due to the invasive nature of these techniques there is an increased risk of mortality and morbidity. Further, invasive techniques can inadvertently impact the state of the skin, which could lead to inaccurate or false results. Even further, invasive techniques are difficult to execute on a large population. The invasive technique may result is discomfort to the participant and may provide a greater potential for infection or other side effects. The present invention provides a non-invasive method for measuring histamine from the skin.

The term "objectively" means without bias or prejudice. Alternatively, any expert or self-assessments are inherently "subjective."

The term "normalization" and/or 'normalized" means the degree to which a population of itch sufferers approach a state of non-itch, or normal, population.

The term "standardization" and/or "standardized" means histamine values expressed relative to the amount of protein measured on the corresponding adhesive or adhesive article. A non-limiting example would be ng histamine/μg soluble protein.

The term "baseline" means information gathered at the beginning of a study from which variations found in the study are measured.

In a further embodiment of the present invention, there are a number of Alternative "Non-Invasive" Sampling Methods that may be used.

Sebutape™: This is a noninvasive approach in that Sebutape™ (acrylic polymer film; CuDerm; Dallas, Tex.) is only very mildly adhesive and may be applied to and removed from even visibly inflamed skin without causing discomfort. Biomarkers recovered/assayed by this technique have included proteins (e.g., cytokines), peptides (e.g., neuropeptides), and small molecule (e.g., nitric oxide) mediators. Historically, this tape is manufactured and sold for sebum collection and can, therefore, be useful for lipid analysis.

D-Squame®: D-Squame® tape is a polyacrylate ester adhesive also manufactured by CuDerm. It may be used to recover the same biomarkers as Sebutape™ but also removes certain epidermal structural proteins (e.g., keratins, involucrin). It has also been used to recover cortisol and serum albumin as systemic inflammatory markers, small molecules and stratum corneum lipids.

Cup Scrubs: Cup scrubs extract proteins directly from the surface of the skin, usually in the presence of buffer and a nonionic surfactant. Cup scrubs are primarily used for recovery of soluble biomarkers such as cytokines, but can also be used to recover small organic molecules. Many more cytokines can be recovered and quantified from cup scrubs than from tape strips. This could be due to several reasons. (a) Due to the presence of detergents and their liquid nature, cup scrubs most likely sample a different protein population than do tape strips. (b) With cup scrubs, cytokines do not have to be further extracted after sample collection since they already are in solution.

Animal (i.e. Dog) Collection Method: D-Squame®: D-Squame™ tape samples are collected on dogs' skin via parting their fur (without shaving). A variety of biomarkers related to skin inflammation, differentiation and barrier integrity can be analyzed from the tapes including total protein, soluble protein, skin multiple analyte profile (skin MAP), skin cytokines and stratum corneum lipids (ceramides, cholesterol, fatty acids).

In an embodiment of the present invention, the present invention provides a method and analysis for non-invasively obtaining a sample for use in isolating histamine In an embodiment, the use of an adhesive device can be used to achieve such sampling. In preparation for such a sampling study for a dandruff sampling, at a baseline visit, a qualified screening grader will complete adherent scalp flaking score (ASFS) grading for each subject and the highest flaking octant will be identified for tape strip sampling. The highest flaking octant will be sampled at baseline and week 3. Tape strips samples will be collected from each subject at each time point (baseline and week 3).

For each subject there will be two tape strip sampling sites both within the same octant (i.e., the highest flaking octant at baseline and week 3) and the scalp is prepared for sampling by appropriate procedures.

The tape strip sampling is repeated additional times, as needed, at the same site placing each D-Squame® tape disc on top of the prior sampled area. The D-Squame® tapes after sample collection are placed into the appropriately labeled wells in a labeled plate.

Following the sampling, an extraction and quantitation procedure is conducted. In an embodiment of the present invention, quantitation of Histamine from extracts of D-Squame® Tape Samples can be conducted using a High Sensitivity Enzyme Immunoassay. (Histamine EIA Kit (US Distributor, Cayman #589651/Histamine EIA kit Manufacture (France), SPbio #A05890)

In this embodiment of the present invention, the sample extraction in preparation for using a Histamine Sensitivity Enzyme assay is: The D-Squame®Tape Samples plates are removed from −80° C. freezer where they are stored following sample collection, and placed place on dry ice. The tape strips are inserted into pre-labeled polypropylene collection tubes, adhesive side facing inward. Appropriate standard extraction buffers are added to each collection tube and then extracted on ice using sonication for 30 min. Each extract solution is isolated from the tape strip and an aliquot of each sample is placed into a specified position of a 96-well polypropylene plate. Aliquots of the extracts of D-Squame® Tape samples are then supplemented with conventional reagents, such as albumin, to help prevent loss of analytes to the walls of labware, transferred into 96-well polypropylene deep well plates and frozen at −80° C. for histamine analysis. A separate aliquot is not supplemented with reagents and is analyzed for soluble protein using a BCA™ Protein Assay Kit, Pierce catalog #23227.

Following the extraction process, histamine standards and controls can be prepared by conventional methods. Histamine will be quantitated with a histamine enzyme immunoassay (EIA) kit from SPI-BIO, distributed by the Cayman Chemical Co. A wash buffer, derivatization reagent, Histamine ACHe tracer and Ellman's Reagent can be prepared by conventional methods. Standards, controls and samples are derivatized in a deep well plate. Plates are washed with buffer and standards, blanks, samples and quality controls are added to the plate and are incubated for 24 hours @ 4° C. Plates are then washed prior to the addition of Elman's reagent and incubation in the dark at room temperature. Plates can be read via standard spectrophotometry. Data analysis is conducted by standard statistical methods and calculations.

In a further embodiment of the present invention, quantization of histamine from extracts of the adhesive article, tape strips, can be conducted using gradient reversed-phase high performance liquid chromatography with tandem mass spectrometry (HPLC/MS/MS).

Tape strips (single or multiple tape strips) obtained from the scalp of human subjects are placed into individual polypropylene vials, each vial is spiked with a stable isotope-labeled histamine ($D_4$-histamine) internal standard (ISTD) and then extracted with acidified water using sonication for 10 min. Each extract solution is isolated from the tape strip and an aliquot of each sample is placed into a specified position of a 96-well polypropylene plate. A set of histamine standards are prepared in the 96-well polypropylene plate over an appropriate calibration range in acidified water and spiked with ISTD. The standards and the extracts of the scalp tape strips are analyzed using gradient reversed-phase high performance liquid chromatography with tandem mass spectrometry (HPLC/MS/MS). Histamine and the ISTD are monitored by positive ion electrospray (ESI) using the selected-reaction-monitoring schemes shown in Table 1. A standard curve is constructed by plotting the signal, defined here as the peak area ratio (peak area histamine/peak area ISTD), for each standard versus the mass of histamine for the corresponding standard. The mass of histamine in the calibration standards and human scalp extract samples are then back-calculated using the generated regression equation. The result can be reported as the mass of histamine/tape strip or the result can be standardized by dividing by the amount of protein that was also found in the tape strip extract. The protein method has been described separately.

TABLE 1

| Compound | Precursor Ion (m/z) | Product Ion (m/z) |
|---|---|---|
| Histamine | 112 | 95 |
| $D_4$-Histamine | 116 | 99 |

Methodology Extension

Although the exact procedure used is described above, there are a number of alternate approaches that could be taken for a number of the steps outlined above that are logical extensions. The extraction solvent employed for isolating histamine from the tape strip can be any appropriate aqueous, organic or organic/aqueous mixture that provides a suitable recovery of histamine. Although a stable isotope-based separation approach was used, a chemical internal standard or an external standard approach could also be employed. LC/MS/MS is generally recognized as the state-of-the-art approach for the quantitative analysis of small organic molecules in biological matrices due to its high selectivity and sensitivity. However, any analytical technique and or other approach providing the required sensitivity and selectivity could be employed. For example, other separation-based approaches such as gas chromatography, liquid chromatography, electrophoresis have been employed. Gas chromatography with sensitive detection modes (ex. mass spectrometry, electron capture, flame ionization) with or without derivitization have been used for the analysis of histamine. High performance liquid chromatography with UV, electrochemical or fluorescence detection, with or without derivitization, have also been employed. Capillary electrophoresis using a variety of detection systems have been evaluated. Similarly, instrumental approaches without separation techniques have also been employed including mass spectrometry, electrochemical and fluorometric assays. Additionally, ligand binding approaches such competitive and non-competitive enzyme linked immunosorbent assays (ELISAs) and radioimmunoassay (RIA) or other labeling schemes have also been employed. Enzyme-based assays have a long history of use in the analysis of histamine. Bioassay using either cell-based or tissue based approaches could have also been used as the means of detection. The measurement of histamine metabolites has also been employed to provide an indirect assessment of histamine levels.

Protein Determination of Tape Strip Extracts:

Histamine levels on tape strip samples of skin measured using a suitable methodology described above can be standardized using amount of protein found in the tape strip extract. Standardization is done by dividing the histamine level by the amount of protein in the tape strip extract.

The amount of protein in the tape strip extract or an equivalent matrix that was used to determine the histamine level on skin can be determined using variety of protein determination methods described in the literature. Examples of such methods include total nitrogen determination, total amino acid determination and protein determination based on any colorimetric, flurometric, luminometric methods. These methods may or may not involve further sample preparation of the tape strip extract prior to protein determination. A non-limiting example of a specific method for protein determination in the tape strip extract is given below. A comprehensive review of protein determination methods, their applicability and limitations are described in the Thermo Scientific Pierce Protein Assay Technical Handbook that can be downloaded from the following link, incorporated by reference herein. www.piercenet.com/Files/1601669_PAssayFINAL_Intl.pdf. Further information related to protein determination can be found at Redinbaugh, M. G. and Turley, R. B. (1986). Adaptation of the bicinchoninic acid protein assay for use with microtiter plates and sucrose gradient fractions. *Anal. Biochem.* 153, 267-271, incorporated by reference herein.

Adhesive tapes sampled from human skin will be extracted and analyzed for protein content using the BCA™ Protein Assay Kit (Pierce). The tape strips sampled from human skin will be extracted with an acidic extraction solution, Following extraction, aliquots of the tape extracts will be transferred into 96-well polypropylene deep well plates and stored at 2-8° C. for protein determination.

The BCA™ Protein Assay Kit is based on the reduction of $Cu^{2+}$ to $Cu^{1+}$ by proteins in an alkaline medium coupled with the sensitive and selective colorimetric detection of $Cu^{+1}$ by bicinchoninic acid (BCA). The purple-colored reaction product, formed by chelation of 2 molecules of BCA with one $Cu^{1+}$ ion, exhibits strong absorbance at a wavelength of 562 nm. The optical density (OD) is measured using a microplate reader. Increasing concentrations of Bovine Serum Albumin (BSA), expressed in micrograms per milliliter (μg/mL), are used to generate a calibration curve in the assay. Appropriate assay QC's prepared from the BSA stock solution will be used to monitor assay performance during sample analysis.

In an alternative embodiment of the present invention, protein determination can be done by direct measurement of protein on an adhesive or an adhesive article such as protein measurement with a SquameScan® 850A (CuDerm Corporation, Dallas, Tex.).

EXAMPLES

Basic Procedure for Histamine Work in Study #1 and Study#2

Dandruff subjects are identified by a qualified grader in two separate clinical studies; study #1 and study #2. Study #2 also includes non-dandruff subjects who are also evaluated at baseline to establish standardized histamine levels (n=121).

Subjects undergo a two week washout period with a conventional non dandruff shampoo without conditioning agents prior to a treatment period with an antidandruff shampoo. Following a three week treatment period with an antidandruff shampoo (a shampoo composition containing zinc pyrithione), a tape strip sample is collected from highest flaking octant as determined at the baseline visit by qualified grader. Scalp tape strips are taken at baseline and after a three week product treatment. Tapes are kept at −80° C. until extracted. A dandruff-involved site is sampled by parting the hair, applying a D-Squame® tape (CuDerm Corporation), and rubbing the tape, as needed. The tape is placed into a pre-labeled 12 well culture dish for storage.

In Study #1, a tape from the surface of the scalp is collected and analyzed by an Enzyme Linked Immunosorbent Assay (ELISA) method. In Study #2, a tape that was one tape below the surface of the scalp is collected and analyzed by gradient reversed-phase high performance liquid chromatography with tandem mass spectrometry (HPLC/MS/MS).

Study #1, samples are extracted with a conventional extraction buffer and sonicated on ice . . . Aliquots of the extracts of DSquame® Tape samples are then supplemented with conventional reagents, such as albumin, to help prevent loss of analytes to the walls of labware, transferred into 96-well polypropylene deep well plates and frozen at −80° C. for histamine analysis. A separate aliquot is not supplemented with reagents and is analyzed for soluble protein using a BCA™ Protein Assay Kit, Pierce catalog #23227.

Study #2, samples are extracted with an acidified water and an aliquot is placed into a 96-well polypropylene plate plates and frozen at −80° C. for histamine analysis.

Study #1, histamine is quantified from extracts of D-Squame® tape samples using a High Sensitivity Enzyme Immunoassay kit from SPIbio, part#A05890 and following the procedure as outlined above.

Study #2, tape strip samples are analyzed by HPLC/MS/MS method as outlined above.

For both studies, histamine concentrations were reported as measured and also as histamine standardized to the amount of soluble protein in the extract as determined by the BCA protein assay as outlined above. Analysis is conducted at baseline and week 3 samples from the antidandruff shampoo treatment group.

Results Summary

Statistical Analysis of Histamine Data: Histamine data was collected on dandruff subjects at both baseline and at week 3 (after treatment) and non-dandruff subjects at baseline. Given the wide variability of histamine levels between subjects as well as within subject (baseline->week 3), it is more efficient to transform the histamine data to the log 10 scale before analysis. Statistical analysis was carried out on the equivalent log 10 Ratio values (i.e., log 10(Week 3/Baseline)). Final reported histamine results are then converted back to their original scale (or % change from baseline values), for ease of interpretation. All statistical analyses were carried out using the SAS JMP (Version 7.0.2) software. A p-value of $\leq 0.10$ (one-sided) was used to determine statistical significance.

The data in FIG. 1 demonstrates that in Study 1 there was a 46% reduction in histamine level following treatment with an antidandruff shampoo over a 3-week periods of time. These histamine levels have been divided by the amount of protein in the tape strip extract.

In an embodiment of the present invention, there may be a 46% reduction in standardized histamine following application with an antifungal shampoo, when compared to a baseline level of histamine prior to the application.

Figure 2:
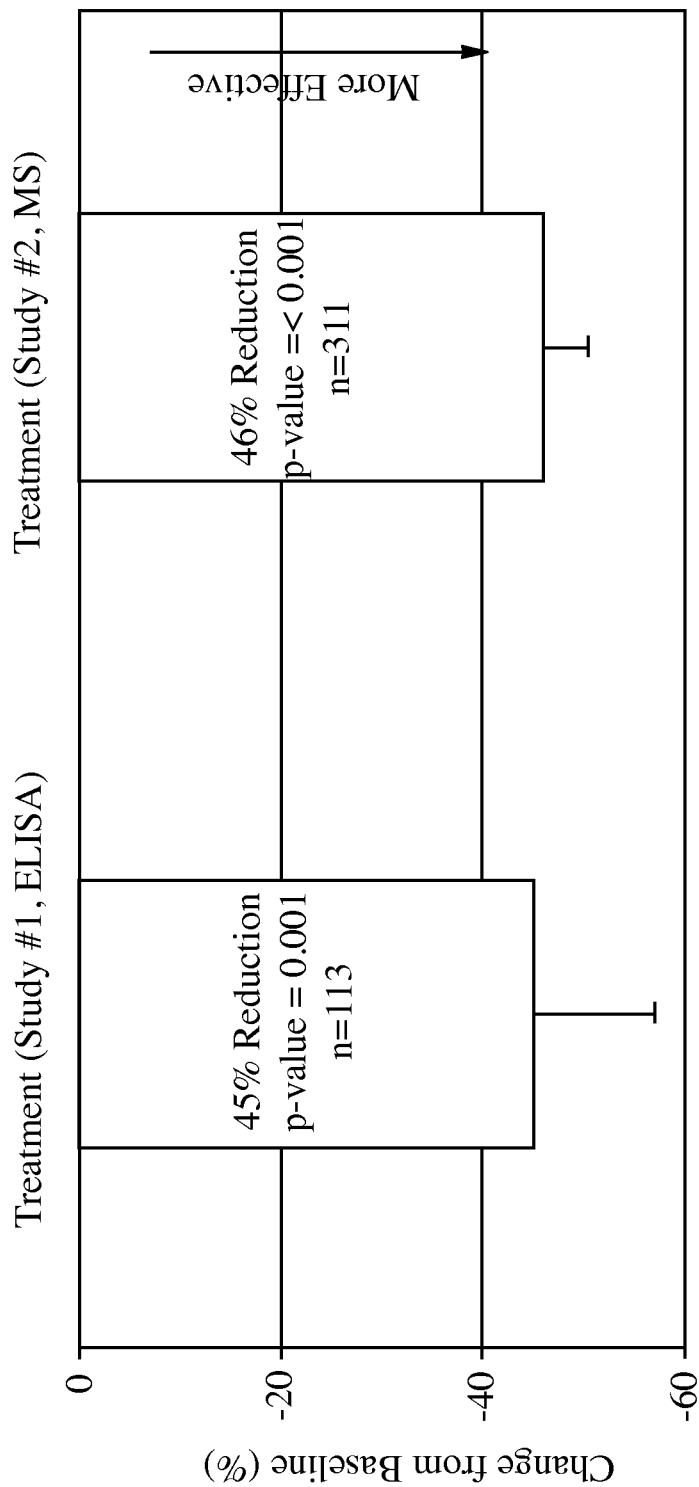
FIG. 2. This figure is a measurement of reduced histamine levels following treatment with an antidandruff shampoo versus baseline.

The data in FIG. 2 demonstrates that an antidandruff shampoo treatment reduced histamine levels by 46% (study #2) and 45% (study #1) versus baseline (p-values=≤0.001, 1-sided). These histamine levels have been divided by the amount of protein in the tape strip extract.

Figure 3:
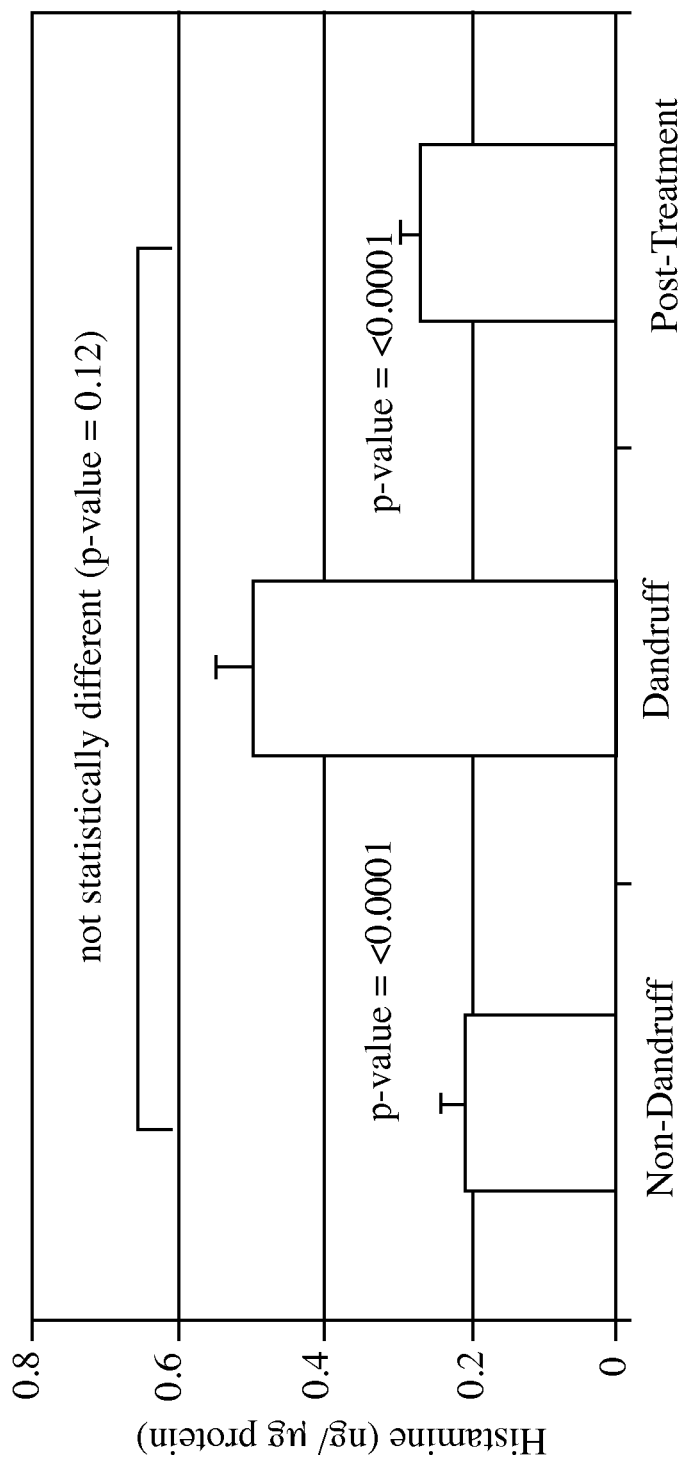
FIG. 3. This figure is a measurement of histamine levels as compared to non-dandruff group and post-treatment with an antidandruff shampoo.

The data in FIG. 3 demonstrates that Dandruff histamine levels were significantly higher than non-dandruff levels (p-value=≦0.0001, 1-sided). Histamine levels on tape strip samples of human scalp measured using a suitable methodology described above can be standardized using amount of protein found in the tape strip extract. Histamine levels were determined from an independent non-dandruff group to establish normal skin histamine levels. Standardization is done by dividing the histamine level by the amount of protein in the tape strip extract. Further this data demonstrates that the antidandruff treatment restored histamine levels to that of the non-dandruff group as discussed above. (1 sided p-value 0.12).

Figure 4:
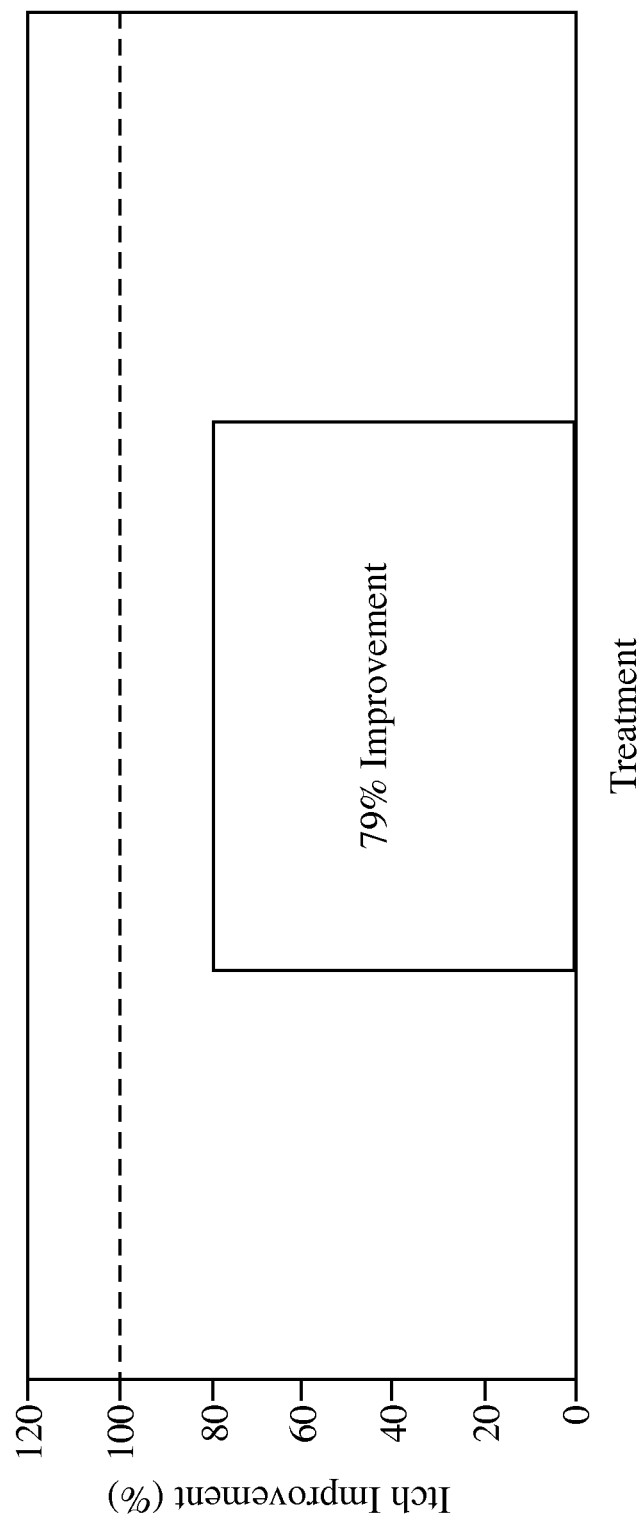
FIG. 4. This figure is a measurement of antidandruff shampoo treatment which has resulted in an improved histamine by 79% relative to non-dandruff levels FIG. 5. This figure is a measurement on a visual analog scale of measurement of itch perception over three week treatment period with an antidandruff shampoo.

The data in FIG. 4 demonstrates that following antidandruff treatment over a 3-week period of time there was an improved histamine level by 79% relative to that of a non-dandruff group. Alternatively, this data demonstrates a 79% return to a healthy skin state. This is a useful means of communicating the benefit as the dandruff population desires a return to a normalized and/or healthy state. This is calculated by dividing the change in histamine levels from baseline to three weeks by the difference between baseline and non-dandruff levels and multiplying by 100.

In an embodiment of the present invention, there is a 79% improvement in itch compared to a normal population. In a further embodiment of the present invention, there is a 79% return to a normalized skin state.

Figure 5:
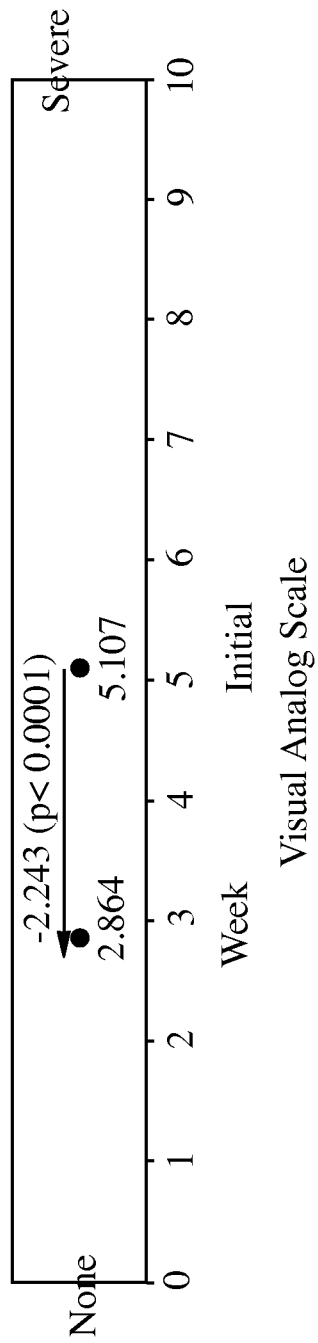
Figure 7:
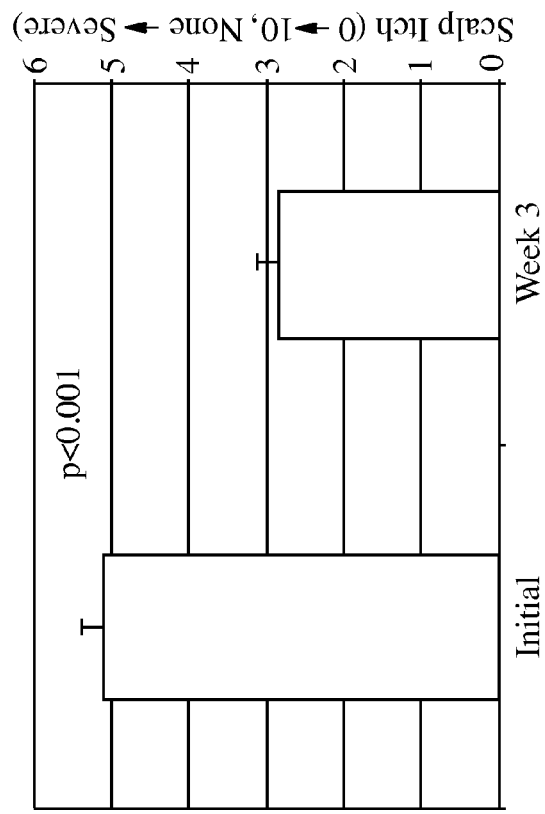
FIG. 6 and FIG. 7. These figures are a side by side direct comparison of histamine measurement from baseline and following three week treatment with antidandruff shampoo via measurement of itch perception measurement from baseline and following three week treatment with antidandruff shampoo.
Figure 6:
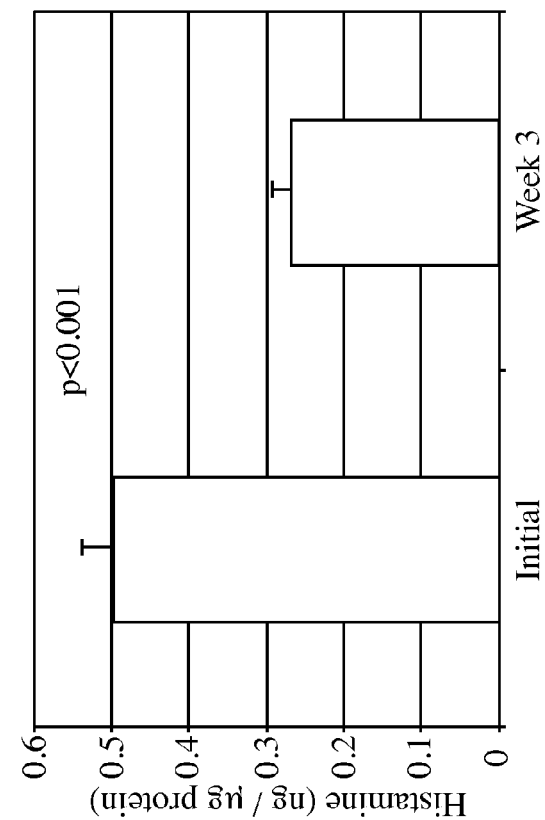

The data in FIG. 5 demonstrates a highly significant reduction in itch perception over a three week treatment period. This would be a subjective measurement based on self-assessment using a visual analog scale. However, the data in FIGS. 6 and 7 provides an objective measure that correlates with the perception of itch wherein the histamine measure (in ng/µg protein) directly correlates with the same population of subject's itch perception data on a visual analog scale. This direct correlation has provided an objective measurement for the perception of itch that was not previously known. Subjective measures are commonly used to assess skin conditions and typically involve either expert graders and/or self-assessment. While these types of measures are useful, they are inherently biased by the evaluator. Objective measures do not have an opportunity for bias and therefore represent more rigorous scientific data.

There may be objective measures of itch which are highly invasive, such as biopsy or blood draw, and thereby have limited use due to the invasive nature of the sampling. Further, there may be low objective measures that are available for measuring itch with low invasive measures, however such measures suffer from being highly subjective. Therefore, the present invention provides a highly objective measure for the perception of itch with low invasiveness which has not been previously known.

In an embodiment of the present invention, the method includes an adhesive article being applied to an epithelieum from a subject afflicted with a disease, disorder or inflammatory reaction. In a further embodiment, the method includes an adhesive article being applied to an epithelium from a subject afflicted with dermatitis. In a further embodiment, the method includes an adhesive article being applied to an epithelium from a subject afflicted with dandruff.

In an embodiment of the present invention, the histamine level may be reduced from 25% to 100%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A non-invasive method for measuring of histamine in an epidermis comprising:
   a) applying an adhesive article to an epithelium of a mammal;
   b) allowing for adherence of epithelial cells to the adhesive article;
   c) removing the adhesive article from the epithelium of the mammal;
   d) preparing the adhesive article including the adhered epithelial cells using standard laboratory methods for histamine extraction;
   e) extracting of histamine from the epithelial cells adhered to said adhesive article;
   f) measuring histamine from the epithelial cells adhered to said adhesive article; and
   g) determining the measured amount of the extracted histamine from the epithelial cells as compared to a baseline sample of histamine in the epithelium of the mammal.

2. The method according to claim 1, wherein the histamine is standardized by dividing the histamine by an amount of protein on the adhesive article.

3. The method according to claim 1, wherein the epithelium comprises stratum corneum.

4. The method according to claim 2 wherein there is a 46% reduction in standardized histamine level following treatment when compared to a baseline level of histamine.

5. The method according to claim 2 wherein the standardized histamine level is reduced from 25% to 100% following treatment when compared to a baseline level of histamine.

6. The method according to claim 2 wherein there is a 46% reduction in standardized histamine following application with an antifungal shampoo, when compared to a baseline level of histamine prior to the application.

7. The method according to claim 2 wherein there is a 46% reduction in standardized histamine following application with an antidandruff shampoo when compared to a baseline level of histamine prior to the application.

8. The method according to claim 2 wherein there is a 46% reduction in standardized histamine following application with a zinc pyrithione shampoo when compared to a baseline level of histamine prior to the application.

9. The method according to claim 1 wherein there is a 79% improvement in itch following an antidandruff treatment when compared to a normal population.

10. The method according to claim 1 wherein there is a 79% return to a normalized skin state following an antidandruff treatment.

11. The method according to claim 1 wherein the mammal is a human.

12. The method according to claim 1 wherein the mammal is non-human.

13. The method of claim 1, wherein the adhesive article is applied to epithelieum from a subject afflicted with a disease, disorder or inflammatory reaction.

14. The method of claim 13 wherein the adhesive article is applied to epithelium from a subject afflicted with dermatitis.

15. The method of claim 13, wherein the adhesive article is applied to epithelium from a subject afflicted with dandruff.

16. A method of objectively measuring the perception of itch in mammals, said method comprising the steps of:
   a) applying as adhesive article to an epithelium of a mammal;
   b) allowing for the adherence of epithelial cells to the adhesive article;
   c) removing the adhesive article from the epithelium of the mammal;
   d) preparing the adhesive article using standard laboratory methods for extraction;
   e) extracting histamine from the epithelial cells adhered to said adhesive article;
   f) measuring histamine from the epithelial cells adhered to said adhesive article; and
   g) determining the amount of histamine in the epithelial cells as compared to a baseline sample.

17. A method according to claim 16 wherein there is a reduction in histamine from a baseline level which is directly proportional to a reduction in an itch perception.

18. A method according to claim 16, wherein the histamine is standardized by dividing the histamine by an amount of protein on the adhesive article.

19. A method of treating the perception of itch of a mammal said method comprising the steps of:
   a) objectively determining perception of itch using method in claim 16;
   b) administering a safe and effective amount of an antifungal compound.

20. A method of treating the perception of itch of a mammal said method comprising the steps of:
   a) objectively determining perception of itch using method in claim 16;
   b) administering a safe and effective amount of an antifungal compound comprising zinc pyrithione.

* * * * *